United States Patent

Baxter et al.

[11] Patent Number: 5,872,146
[45] Date of Patent: Feb. 16, 1999

[54] MERCAPTO ALKYL PEPTIDYL COMPOUNDS HAVING MMP AND TNF INHIBITORY ACTIVITY

[75] Inventors: Andrew Douglas Baxter; John Gary Montana; David Alan Owen, all of Cambridge, United Kingdom

[73] Assignee: Chiroscience Limited, United Kingdom

[21] Appl. No.: 832,929

[22] Filed: Apr. 4, 1997

[30] Foreign Application Priority Data

Apr. 4, 1996 [GB] United Kingdom .................. 9607120

[51] Int. Cl.[6] .................. A61K 31/40; C07D 209/48
[52] U.S. Cl. .................. 514/417; 548/477
[58] Field of Search .................. 548/477; 514/417

[56] References Cited

FOREIGN PATENT DOCUMENTS

| 9506031 | 3/1995 | WIPO . |
|---|---|---|
| 9513289 | 5/1995 | WIPO . |
| 49611209 | 4/1996 | WIPO . |
| 9635714 | 11/1996 | WIPO . |
| 97/03783 | 2/1997 | WIPO . |

OTHER PUBLICATIONS

Ahlmquist, R.G. et al., (1992) "Development of Peptidomimetic Inhibitors of a Newly Isolated Altrail Peptide–Degrading Enzyme," In Peptides: Chemistry and Biology, as referred to in *Proceedings of the American Peptide Symposium,* Cambridge, Jun. 16–21, 1991, pp. 791–792.

*Primary Examiner*—Laura L. Stockton
*Attorney, Agent, or Firm*—Saliwanchik, Lloyd & Saliwanchik

[57] ABSTRACT

Described herein are compounds of formula (I):

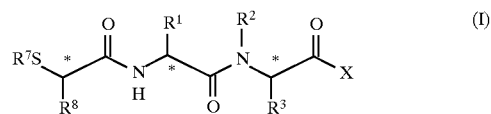

which have MMP and TNF inhibitory activity.

22 Claims, No Drawings

MERCAPTO ALKYL PEPTIDYL COMPOUNDS HAVING MMP AND TNF INHIBITORY ACTIVITY

FIELD OF THE INVENTION

This invention relates to a novel class of peptidyl derivatives, to processes for their preparation, and to their use in medicine.

BACKGROUND OF THE INVENTION

Metalloproteinases, including matrix metalloproteinase (MMP), (human fibroblast) collagenase, gelatinase and TNF convertase (TACE), and their modes of action, and also inhibitors thereof and their clinical effects, are described in WO-A-9611209, PCT/GB96/02438 and PCT/GB96/02892, the contents of which are incorporated herein by reference. MMP inhibitors may also be useful in the inhibition of other mammalian metalloproteinases such as the adamalysin family (or ADAMs) whose members include TNF convertase (TACE) and ADAM-10, which can cause the release of TNFα from cells, and others, which have been demonstrated to be expressed by human articular cartilage cells and also involved in the destruction of myelin basic protein, a phenomenon associated with multiple sclerosis.

Compounds which have the property of inhibiting the action of metalloproteinases involved in connective tissue breakdown, such as collagenase, stromelysin and gelatinase, have been shown to inhibit the release of TNF both in vitro and in vivo. See Gearing et al (1994), Nature 370:555–557; McGeehan et al (1994), Nature 370:558–561; GB-A-2268934; and WO-A-9320485. All of these reported inhibitors contain a hydroxamic acid zinc-binding group, as do the imidazole-substituted compounds disclosed in WO-A-9523790. Other compounds that inhibit MMP and/or TNF as described in WO-A-9513289, WO-A-9611209, WO-A-96035687, WO-A-96035711, WO-A-96035712 and WO-A-96035714.

SUMMARY OF THE INVENTION

The invention encompasses novel mercaptoalkylpeptidyl compounds of formula (I) which am useful inhibitors of matrix metalloproteinases and/or TNFα-mediated diseases including degenerative diseases (such as defined above) and certain cancers.

Novel compounds of the invention are of general formula (I):

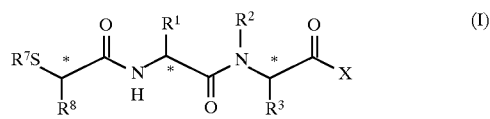

wherein:

$R^1$ is a $C_{1-6}$ alkyl, $C_{2-6}$ alkenyl, ($C_{1-6}$ alkyl) aryl, aryl, $C_{1-6}$ alkylheteroaryl, heteroaryl or $C_{1-6}$ alkyl-$AR^9$ group where A is O, $NR^9$ or $S(O)_m$ where m=0–2, and $R^9$ is H, $C_{1-4}$ alkyl, aryl, heteroaryl, ($C_{1-4}$ alkyl)aryl or ($C_{1-4}$ alkyl)heteroaryl; if A=$NR^9$ the groups $R^9$ may be the same or different;

$R^2$ is hydrogen or a $C_{1-6}$ alkyl group;

$R^3$ is $C_{1-6}$ alkyl-$R^6$, aryl-$R^6$, heteroaryl-$R^6$, cyclo($C_{3-6}$) alkyl-$R^6$, $C_{1-6}$ alkyl-aryl-$R^6$, $C_{1-6}$ alkyl-heteroaryl-$R^6$ or $C_{1-6}$ alkyl-cyclo($C_{3-6}$)alkyl-$R^6$, and $R^6$ is an amidino or guanidino group;

X is $NR^4R^5$ where $R^4$ is hydrogen, aryl, heteroaryl, $C_{1-6}$ alkyl-heteroaryl, cyclo($C_{3-6}$)alkyl, $C_{1-6}$ alkyl-cyclo($C_{3-6}$) alkyl, heterocyclo($C_{4-6}$)alkyl (such as pyrrolidine or piperidine) or $C_{1-6}$ alkyl-heterocyclo($C_{4-6}$)alkyl, and $R^5$ is hydrogen or $C_{1-6}$ alkyl group, or $NR^4R^5$ is a ring such as pyrrolidino, piperidino or morpholino;

$R^7$ is hydrogen or $R^{10}CO$ where $R^{10}$ is $C_{1-4}$ alkyl, $C_{1-4}$ alkylaryl, $C_{1-4}$ alkylheteroaryl, cyclo($C_{3-6}$)alkyl, $C_{1-4}$ alkyl-cyclo($C_{3-6}$)alkyl, $C_{3-6}$ alkenyl, $C_{3-6}$ alkenylaryl, aryl or heteroaryl;

$R^8$ is aryl (substituted with $R^{11}$), heteroaryl (optionally substituted with $R^{11}$), $C_{1-4}$ alkyl-$R^{11}$, $C_{1-4}$ alkylaryl (substituted with $R^{11}$), $C_{1-4}$ alkylheteroaryl (optionally substituted with $R^{11}$), cyclo ($C_{3-6}$) alkyl (optionally substituted with $R^{11}$), cyclo($C_{3-6}$)alkenyl (optionally substituted with $R^{11}$) or $C_{1-4}$ alkyl-cyclo($C_{3-6}$)alkyl (optionally substituted with $R^{11}$), the groups

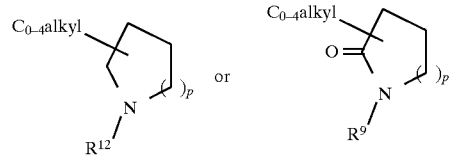

where p=1–2, the group

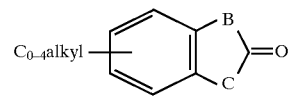

where B and C are each selected from O, S, $C(R^9)_2$ or $NR^9$ and these may be the same or different;

$R^{11}$ is $SO_2R^{10}$, $SO_2N(R^9)_2$ (in which each $R^9$ is the same or different), $SR^7$, $COR^{13}$, $N(R^9)_2$, $NR^9R^{12}$, $OR^9$, succinimido or phthalimido;

$R^{12}$ is hydrogen or a $COR^9$, $CO_2R^9$ (where $R^9$ is not H), $CONHR^9$, or $SO_2R^9$ (where $R^9$ is not H) group; and $R^{13}$ is a OH, $OC_{1-4}$ alkyl, $OC_{1-4}$ alkylaryl, $N(R^9)_2$ (in which $R^9$ is the same or different), $C_{1-4}$ alkyl, aryl, heteroaryl, $C_{1-4}$ alkylaryl or $C_{1-4}$ alkylheteroaryl;

and the salts, solvates and hydrates thereof.

Combinations of substituents and/or variables are only permissible if such combinations result in stable compounds.

DESCRIPTION OF THE INVENTION

Preferred compounds of the invention are those wherein any one or more of the following apply:

$R^1$ is $C_{1-6}$ alkyl or $C_{1-6}$ alkyl-$AR^9$, and A is O or $S(O)_{0-2}$;

$R^2$ is H;

$R^3$ is $C_{1-6}$ alkyl-$R^6$, aryl-$R^6$ or $C_{1-6}$ alkylaryl-$R^6$;

$R^4$ is aryl, heteroaryl or $C_{1-6}$ alkylheteroaryl;

$R^5$ is H, $R^8$ is $C_{1-3}$ alkyl-$R^{11}$ or $C_{3-4}$ alkyl-$COR^{13}$;

$R^9$ is H, $C_{1-6}$ alkyl or $C_{1-4}$ alkylaryl;

$R^{10}$ is $C_{1-4}$ alkyl or aryl;

$R^{12}$ is succinimido or phthalimido; and $R^{13}$ is OH or $OC_{1-4}$ alkyl.

The compounds of the examples are particularly preferred.

It will be appreciated that the compounds according to the invention can contain one or more asymmetricallysubstituted carbon atoms, for example those marked with an asterisk in formula (I). The presence of one or more of these asymmetric centres in a compound of formula (I) can give rise to stereoisomers, and in each case the invention is to be understood to extend to all such stereoisomers, including enantiomers and diastereomers, and mixtures including racemic mixtures thereof.

In the formulae herein, the ⁻ line is used at a potential asymmetric centre to represent the possibility of R- and S-configurations, the < line and the . . . line to represent a unique configuration at an asymmetric centre.

As used in this specification, alone or in combination, the term "$C_{1-6}$ alkyl" refers to straight or branched chain alkyl moiety having from one to seven carbon atoms, including for example, methyl, ethyl, propyl, isopropyl, butyl, tert-butyl, pentyl, hexyl and the like The term "$C_{1-6}$ alkyl" refers to a straight or branched chain alkyl moiety having from one to four carbon atoms, including for example, methyl, ethyl, propyl, isopropyl, butyl, tert-butyl and the like.

The term "$C_{2-6}$ alkenyl" refers to a straight or branched chain alkyl moiety having two to six carbon atoms and having in addition one double bond, of either E or Z stereochemistry where applicable. This term would include for example, vinyl, 1-propenyl, 1- and 2-butenyl, 2-methyl-2-propenyl etc.

The term "cyclo($C_{3-6}$)alkyl" refers to a saturated alicyclic moiety having from three to six carbon atoms and includes for example cyclopropyl, cyclobutyl, cyclopentyl, cyclohexyl and the like.

The term "heterocyclo($C_{4-6}$)alkyl" refers to a saturated heterocyclic moiety having from three to six carbon atoms and one or more heteroatom from the group N, O, S and includes for example azetidinyl, pyrrolidinyl, tetrahydrofuranyl, piperidinyl and the like.

The term "cyclo($C_{4-6}$)alkenyl" refers to an alicyclic moiety having from three to six carbon atoms and having in addition one double bond. This term would include for example cyclopentenenyl or cyclohexenyl.

The term "aryl" means an optionally substituted phenyl or naphthyl group with the substituent(s) being selected, for example, from halogen, trifluoromethyl, $C_{1-6}$ alkyl, alkoxy, phenyl and the like.

The term "heteroaryl" refers to aromatic ring systems of five to ten atoms or which at least one atom is selected from the group, O, N, or S and includes for example furanyl, thiophenyl, pyridyl, indolyl, quinolyl and the like.

The term "alkoxy" refers to a straight chain or branched chain alkoxy group containing a maximum of six carbon atoms, such as methoxy, ethoxy, propoxy, isopropoxy, butoxy, tert-butoxy and the like.

The term "$C_{0-4}$alkyl" refers to a straight or branched chain alkyl moiety having from zero to four carbon atoms, including for example, methyl, ethyl, propyl, isopropyl and the like.

The term "halogen" means fluorine, chlorine, bromine or iodine.

The terms "protected amino" and "protected carboxy" mean amino and carboxy groups which are protected in a manner familiar to those skilled in the art. For example, an amino group can be protected by a benzyloxycarbonyl, tert-butoxycarbonyl, acetyl or like groups, or in the form of a phthalimido or like group. A carboxyl group can be protected in the form of a readily cleavable ester such as the methyl, ethyl, benzyl or tert-butyl ester.

Salts of compounds of formula (I) include pharmaceutically acceptable salts, for example acid addition salts derived from inorganic or organic acids, such as hydrochlorides, hydrobromides, p-toluenesulphonates, phosphates, sulphates, perchlorates, acetates, trifluoroacetates, propionates, citrates, malonates, succinates, lactates, oxalates, tartrates and benzoates.

Salts may also be formed with bases. Such salts include salts derived from inorganic or organic bases, for example alkali metal salts such as magnesium or calcium salts, and organic amine salts such as morpholine, piperidine, dimethylamine or diethylamine salts.

When the "protected carboxy" group in compounds of the invention is an esterified carboxyl group, it may be a metabolically labile ester of formula $CO_2R^{14}$ where $R^{14}$ may be an ethyl, benzyl, phenethyl, phenylpropyl, α- or β-naphthyl, 2,4-dimethylphenyl, 4-tert-butylphenyl, 2,2,2-trifluoroethyl, 1-(benzyloxy)benzyl, 1-(benzyloxy)ethyl, 2-methyl-1-propionyloxypropyl, 2,4,6-trmethylbenzyloxymethyl or pivaloyloxymethyl group.

Compounds of the general formula (I) may be prepared by any suitable method known in the art and/or by the following processes.

It will be appreciated that, where a particular stereoisomer of formula (I) is required, the synthetic processes described herein may be used with the appropriate homochiral starting material and/or isomers maybe resolved from mixtures using conventional separation techniques (e.g. HPLC).

The compounds according to the invention may be prepared by the following process. In the description and formulae below the groups $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, A, B, C and X are as defined above, except where otherwise indicated. It will be appreciated that functional groups, such as amino, hydroxyl or carboxyl groups, present in the various compounds described below, and which it is desired to retain, may need to be in protected form before any reaction is initiated. In such instances, removal of the protecting group may be the final step in a particular reaction. Suitable protecting groups for such functionality will be apparent to those skilled in the art. For specific details see Greene et at "Protective Groups in Organic Synthesis", Wiley Interscience.

A process for preparing compounds of general formula (I) comprises deprotecting (for example by hydrolysis) a compound of general formula (II)

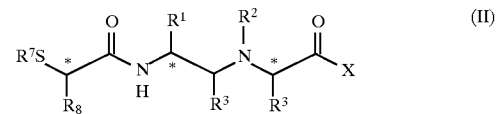

wherein $R^7$ represents a suitable protecting group (e.g. tert-butyl, trityl, benzoyl or acetate).

It will be appreciated that where a particular stereoisomer of formula (I) is required, this may be obtained by conventional resolution techniques such as high performance liquid chromatography. Where desired, however, appropriate homochiral starting materials may be used in the coupling reaction to yield a particular stereoisomer of formula (I). This is exemplified below.

Intermediates of general formula (II) may be prepared by coupling an acid of the formula $R^7S$—$CHR^8$—$COOH$ (III) wherein $R^7$ and $R^8$ are as defined above, or an active derivative thereof, with an amine of the formula $H_2N$—$CHR^1$—$CO$—$NR^2$—$CHR^3$—$COX$(IV). Active derivatives of acids of formula (III) include for example acid anhydrides or acid halides, such as acid chlorides.

The coupling reaction may be performed using standard conditions for amination reactions of this type. Thus, the reaction may be achieved in a solvent, for example an inert organic solvent such as an ether, e.g. a cyclic ether such as tetrahydrofuran, an amide e.g. a substituted amide such as dimethylformamide, or a halogenated hydrocarbon such as dichloromethane at a low temperature e.g. −30° C. to ambient temperature, such as −2° C. to 0° C., optionally in the presence of as base, e.g. an organic base such as an amine, e.g. triethylamine or a cyclic amine such as N-methylmorpholine. Where an acid of formula (III) is used, the reaction may additionally be performed in the presence of a condensing agent, for example a diimide such as N,N'-dicyclohexylcarbodiimide, advantageously in the presence of a triazole such as 1-hydroxybenzotriazole. Alternatively, the acid may be reacted with a chloroformate for example ethyl chloroformate, prior to reaction with the amine of formula (IV).

An amine of general formula (IV) may be prepared by coupling an acid of the formula $H_2N—CHR^1—COOH$ (V) or an active derivative thereof, with an amine of the formula $R^2—NH—CHR^3—COX$ (VI), followed by removal of any protecting groups. Active derivatives of acids for formula (V) include for example acid anhydrides or acid halides such as acid chlorides as outlined earlier.

Amino acids and their derivatives as depicted by general formulae (V) and (VI) can be obtained in chiral or racemic form. In the chiral form they provide asymmetric building blocks for the chiral synthesis of compounds of general formula (I). Many of these derivatives can be readily obtained from commercially available starting materials using methods known to those skilled in the art. See "The Practice of Peptide Synthesis" by M. Bodanszk et al, Springer Verlag, New York (1984) and WO-A-9221360.

Compounds of general formula (II) may also be prepared by nucleophilic substitution of compounds of general formula (VII).

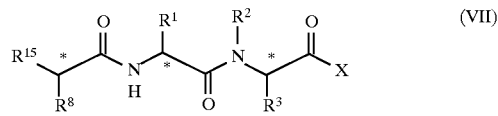

wherein $R^{15}$ represents a suitable leaving group (e.g. a halogen such as bromide, or an alkylsulphonate such as methanesulphonate) with a thiol of the formula $R^7SH$ (VII) wherein $R^7$ represents a suitable protecting group (e.g. tert-butyl, trityl, benzoyl or acetate), using standard conditions known to those skilled in the art; see WO-A-9005719.

Thiols of general formula (VII) may be obtained from commercially available starting materials using methods known to those skilled in the art. Many thiols of general formula (VIII) are also commercially available.

Compounds of general formula (VII) may be prepared by coupling an acid of general formula (IX).

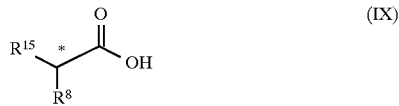

wherein $R^{15}$ and $R^8$ are as defined above (or suitably protected versions thereof) or an active derivative thereof, with an amine of formula (IV) using similar coupling conditions to those described for the preparation of compounds of formula (II).

Carboxylic acids of the structure depicted in formulae (III) and (IX) can be obtained in chiral or racemic form. Many of these derivatives can be readily obtained from commercially available starting materials using methods known to those skilled in the art; see WO-A-9005719.

Intermediates of general formula (II) may also be prepared by coupling an acid of formula (X)

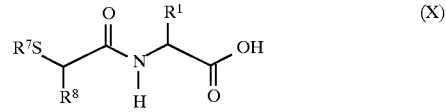

wherein $R^1$, $R^7$ and $R^8$ are as defined above, or an active derivative thereof, with an amine of formula (VI) by the procedure described previously.

Acids of general formula (X) may in turn be prepared by coupling an acid of formula (III), or an active derivative thereof with an amine of formula (V).

Active derivatives of acids of formula (III) include for example acid anhydrides or acid halides such as acid chlorides as outlined earlier.

Compounds of formula (I) may also be prepared by interconversion of other compounds of formula (I). Thus for example, a compound of formula (I) wherein $R^1$ is a $C_{1-6}$ alkyl group may be prepared by hydrogenation (using palladium on carbon in suitable solvent, such as an alcohol— e.g. ethanol) of a compound of formula (I) who $R^1$ is a $C_{2-6}$ alkenyl group. A further example would include a compound of formula (I) wherein $R^7$ is a group $R^{10}$ CO may be prepared by acylation (using a suitable acid chloride $R^{10}$ COCl, in the, presence of a base such as a triethylamine in a suitable solvent, such as a chlorinated solvent—e.g. dichloromethane) of a compound of formula (I) wherein $R^7$ is H.

Any mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances.

The compounds according to the invention exhibit in vitro inhibiting activities with respect to stromelysin, collagenase and gelatinase. Compounds according to the invention also exhibit in vitro inhibition of TNF release. The activity and selectivity of the compounds may be determined by use of the appropriate enzyme inhibition test, for example as described in WO-A-9611209 and PCT/GB96/02892.

This invention also relates to a method of treatment for patients including man and/or mammalian animals raised in the dairy, meat or fur industries or as pets) suffering from disorders or diseases which can be attributed to stromelysin as previously described and, more specifically, a method of treatment involving the administration of the matrix metalloproteinase inhibitors of formula (I) as the active constituents.

Accordingly, the compounds of formula (I) can be used among other things in the treatment of osteoarthritis and rheumatoid arthritis, and in diseases and indications resulting from the over-expression of these matrix metalloproteinases such as found in certain metastatic tumour cell lines.

As mentioned above, compounds of formula (I) are useful in human or veterinary medicine since they are active as inhibitors of TNF and MMPs. Accordingly in another aspect, this invention concerns:

a method of management (by which is meant treatment of prophylaxis) of disease or conditions mediated by TNF, L-selectin sheddase and/or MMPs in mammals, in particular in humans, which method comprises administering to the mammal an effective, amount of a compound of formula (I) above, or a pharmaceutically acceptable salt thereof; and a compound of formula (I) for use in human or veterinary medicine, particularly in the management (by which is meant treatment or prophylaxis) of diseases or conditions mediated by TNF, L-selectin sheddase and/or MMPs; and the use of a compound of formula (I) in the preparation of an agent for the management (by which is meant treatment or prophylaxis) of diseases or conditions mediated by TNF, L-selectin sheddase and/or MMPs.

The disease or conditions referred to above include inflammatory diseases, autoimmune diseases cancer, cardiovascular diseases, diseases involving tissue breakdown such as rheumatoid arthritis, osteoarthritis, osteoporosis, neurodegeneration, Alzheimer's disease, atherosclerosis, congestive heart failure, stroke, vasculitis, Crohn's disease, ulcerative colitis, multiple sclerosis, periodontitis, gingivitis and those involving tissue breakdown such as bone resportion, haemorrhage, coagulation, acute phase response, cachexia and anorexia, acute infections, HIV infections, fever, shock states, graft versus host reactions, dermatological conditions, surgical wound healing, psoriasis, atopic dermatitis, epidermolysis bullosa, tumour growth, angiogenesis and invasion by secondary metastases, ophthalmological disease, retinopathy, corneal ulceration, reperfusion injury, migraine, meningitis, asthma, rhinitis, allergic conjunctivitis, eczema, anaphylaxis, restenosis, congestive heart failure, endometriosis, atherosclerosis and endosclerosis, malignant ascitis, malignant pleural effusion, cerebral ischaemia, ischaemic heart disease, and chronic ulcers.

For the treatment of rheumatoid arthritis, osteoarthritis, and in diseases and indications resulting from the overexpression of matrix metalloendoproteinases such as found in certain metastatic tumour cell lines or other diseases mediated by the matrix metalloendoproteinases or increased TNF production, the compunds of formula (I) may be administered orally, topically, parenterally, by inhalation spray or rectally in dosage unit formulations containing non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats etc, the compounds of the invention are effective in the treatment of humans.

The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules where in the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate polyvinyl-pyrrolidone, gum tragacanth and gum acacia; dispersing or wetting agents may be a naturally occuring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters dervied from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavouring and colouring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally occuring gums, for example gum acacia or gum tragacanth, naturally-occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example gycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rental temperature and will therefore melt in the rectum to release the drug. Such materials are cocoa butter and polyethylene glycols.

For topical use, creams, ointments, jellies, solutions or suspensions, etc containing the compounds of Formula (I) are employed (For purposes of this, application, topical application shall include mouth washes and gargles.)

Dosage levels of the order of from about 0.05 mg to about 140 mg per kilogram of body weight per day are useful in the treatment of the above-indicated conditions (about 2.5 mg to about 7 g per patient per day). For example, inflammation may be effectively treated by the administration of from about 0.01 to 50 mg of the compound per kilogram of body weight per day (about 0.5 mg to about 3.5 g per patient per day).

The amount of active ingredient that may be combined with the carrier materials to produce a single dosage form will vary depending upon the host treated and the particular mode of administration. For example, a formulation intended for the oral administration of humans may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy.

The following Examples illustrate the invention.

INTERMEDIATE 1

1-N-α-(9-Fluorenylmethoxycarbonyl)-N-ω'-(pentamethylchromanyl)-L-arginyl-rink amide AM resin Rink amide AM resin (1.0 g, 0.55 mmol substitution) was washed with anhydrous dimethylformamide (5×20 ml). After removal of solvent, a solution of N-α-(9-fluorenylmethoxycarbonyl)-N-ω'-(pentamethylchromanyl)-L-arginine (1.456 g, 2.2 mmol), 2-(1H-benzotriazol-1-yl)-1,1,3,3-tetramethyluronium hexafluorophosphate (0.833 g, 2.2 mmol) and 1-hydroxybenzotriazole (297 mg, 2.2 mmol) in dimethylformamide (25 ml) was added to the resin. Diisopropylethylamine (4.4 mmol, 0.568 ml) was added immediately and the reaction agitated for 2 hr at RT. The resin was then washed with dimethylformamide (5×20 ml), dichloromethane (2×20 ml), methanol (2×20 ml) and finally dichloromethane (3×20 ml).

INTERMEDIATE 2

2-L-Arginyl(N-ω'-pentamethylchromanyl)-rink amide AM resin

Intermediate 1 was treated with two charges of a 20% (v/v) piperidine in dimethylformamide solution for 30 min at RT. The resin was washed with dimethylformamide, methanol and dichloromethane.

INTERMEDIATE 3

N-α-(9-Fluorenylmethoxycarbonyl)-L-leucyl-L-arginyl(N-ω'-pentamethylchromanyl)-rink amide AM resin A solution of N-α-(9-Fluorenylmethoxycarbonyl)-L-leucine (77.7 mg, 0.22 mmol, 2-(1H-benzotriazol-1-yl)-1,1,3,3-tetramethyluronium hexafluorophosphate (83.3 g, 0.22 mmol) and 1-hydroxybenzotriazole (29.7 mg, 0.22 mmol) in dimethylformamide (25 ml) was added to Intermediate 2 (0.1 g, 0.055 mmol equivalent). Diisopropylethylamine (0.44 mmol, 0.0568 ml) was added immediately and the reaction agitated for 2 hr at RT. The solvent was then removed by filtration, and the resin washed with dimethylformamide, methanol and dichloromethane.

Similarly prepared were:

INTERMEDIATE 4

N-α(9-Fluorenylmethoxycarbonyl)-L-isoleucyl-L-arginyl(N-ω'-pentamethylchromanyl)rink amide AM resin From N-α-(9-fluorenylmethoxycarbonyl)-L-isoleucine (77.7 mg, 0.22 mmol and Intermediate 2 (0.1 g, 0.055 mmol equivalent).

INTERMEDIATE 5

N-α-(9-Fluorenylmethoxycarbonyl)-L-norvalyl-L-arginyl(N-ω'-pentamethylchromanyl)-rink amide AM resin From N-α-(9-fluorenylmethoxycarbonyl)-L-norvaline (74.6 mg, 0.22 mmol) and Intermediate 2 (0.1 g, 0.055 mmol equivalent).

INTERMEDIATE 6

N-α-(9-Fluorenylmethoxycarbonyl)-L-valyl-L-arginyl(N-ω'-pentamethylchromanyl)-rink amide AM resin From N-α-(9-fluorenylmethoxycarbonyl)-L-valine (74.6 mg, 0.22 mmol) and Intermediate 2 (0.1 g, 0.055 mmol equivalent).

INTERMEDIATE 7

L-Leucyl-L-arginyl(N-ω'-pentamethylchromanyl)-rink amide AM resin

From Intermediate 3 (0.1 mg, 0.055 mmol equivalent) which was treated twice with a fresh solution of 20% (v/v) piperidine in dimethylformamide.

Similarly prepared were:

INTERMEDIATE 8

L-Isoleucyl-L-arginyl(N-ω'-pentamethylchromanyl)-rink amide AM resin

From Intermediate 4 (0.1 mg, 0.055 mmol equivalent).

INTERMEDIATE 9

L-Norvalyl-L-arginyl(N-ω'-pentamethylchromanyl)-rink amide AM resin

From Intermediate 5 (0.1 mg, 0.055 mmol equivalent).

INTERMEDIATE 10

L-Valyl-L-arginyl(N-ω'-pentamethylchromanyl)-rink amide AM resin

From Intermediate 6 (0.1 mg, 0.055 mmol equivalent).

INTERMEDIATE 11

2-Triphenylmethylmercapto-5-phthalimidopentanoic acid

Trityl chloride (28 g, 100 mmol) was dissolved in anhydrous acetonitrile (250 ml), and diisopropylethylamide (12.9 ml, 100 mmol) was added, 2-Bromo-5-phthalimidopentanoic acid (6.25 g, 100 mmol) in anhydrous acetonitrile (50 ml) was then added, and the reaction allowed to proceed for 48 hr at RT. After this, the solvent was removed under reduced pressure and the resulting residue was added to a 10% NaHCO$_3$/diethyl ether (4:1) mixture. The NaHCO$_3$ layer was washed a further two times with diethyl ether and then acidified to pH 2.5 with 10% NaHSO$_4$. The resulting precipitate was washed with NaHSO$_4$ and redissolved in ethyl acetate. The ethyl acetate solution was washed with brine and dried (MgSO$_4$). After filtration, the solvent was evaporated in vacuo to give the title compound as a pale beige solid (32.4 g, 96%). TLC R$_f$ 0.45 (Cyclohexane:ethyl acetate 1.1).

INTERMEDIATE 12

N-(2-Triphenylmethylmercapto-5-phthalimidopentanoyl)-L-leucyl-L-arginyl(N-ω'-pentamethylchromanyl)-rink amide AM resin A solution of Intermediate 11 (73.4 mg, 0.22 mmol), 2-(1H-benzotriazol-yl)-1,1,3,3-tetramethyluronium hexafluorophosphate (83.3 mg, 0.22 mmol) and 1-hydroxybenzotriazole (29.7 mg, 0.22 mmol) in dimethylformamide (25 ml) was added to Intermediate 7 (0.1 g, 0.055 mmol equivalent). Diisopropylethylamine (0.44 mmol, 0.0568 ml) was added immediately and the reaction agitated for 2 hr at RT. The solvent was then removed by filtration, and the resin washed with dimethylformamide, methanol and dichloromethane. The resin was then dried overnight in a vacuum desiccator.

Similarly prepared were:

INTERMEDIATE 13

N-(2-Triphenylmethylmercapto-5-phthalimidopentanoyl)-L-isoleucyl-L-arginyl(N-ω'-pentamethylchromanyl)-rink amide AM resin From Intermediate 11 (73.4 mg, 0.22 mmol) and Intermediate 8.

INTERMEDIATE 14

N-(2-Triphenylmethylmercapto-5-phthalimidopentanoyl)-L-norvalyl-L-arginyl(N-ω'-pentamethylchromanyl)-rink amide AM resin From Intermediate 11(73.4 mg, 0.22 mmol) and Intermediate 9.

INTERMEDIATE 15

N-(2-Triphenylmethylmercapto-5-phthalimidopentanoyl)-L-valyl-L-arginyl(N-ω'-pentamethylchromanyl)-rink amide AM resin From Intermediate 11 (73.4 mg, 0.22 mmol) and Intermediate 12.

EXAMPLE 1

N-(2-mercapto-5-phthalimidopentanoyl)-L-leucyl-L-argininamide

Intermediate 12 (0.1 g, 0.055 mmol) was treated with dichloromethane containing 5% (v/v) trifluoroacetic acid and 5% (v/v) triisopropylsilane (10 ml) for 30 min at RT. This solution was removed by filtration and washed with dichloromethane. The resin was then treated twice with a solution of trifluoroacetic acid containing 2.5% (v/v) triisopropylsilane, 2.5% anisole and 2.5% ethanedithiol (1 ml) for 2 hr at RT. The filtrates were pooled and the solvent removed under reduced pressure. The resultant oil was triturated immediately with ice-cold dry diethyl ether and the precipitate was isolated by centrifugation and washed copiously with dry diethyl ether. After evaporation in vacuo, the title compound was obtained as an off-white solid (14.5 mg, 72.5%).

Similarly prepared were:

EXAMPLE 2

N-(2-mercapto-5-phthalimidopentanoyl)-L-isoleucyl-L-argininamide

From Intermediate 13 (0.1 g, 0.055 mmol equivalent) as an off-white solid (18.8 mg, 94%).

EXAMPLE 3

N-(2-mercapto-5-phthalimidopentanoyl)-L-norvalyl-L-argininamide

From Intermediate 14 (0.1 g, 0.055 mmol equivalent) as an off-white solid (17.6 mg, 91.4%).

EXAMPLE 4

N-(2-mercapto-5-phthalimidopentanoyl)-L-valyl-L-argininamide

From Intermediate 15 (0.1 g, 0.055 mmol equivalent) as an off-white solid (15.7 mg, 81.5%).

We claim:

1. A compound of general formula (I):

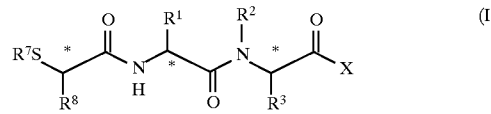

wherein:

R$^1$ is selected from the group consisting of C$_{1-6}$ alkyl, C$_{2-6}$ alkenyl, (C$_{1-6}$ alkyl)aryl, aryl, and C$_{1-6}$ alkyl-AR$^9$ where A is selected from the group consisting of O, NR$^9$, and S(O)$_m$ where m=0–2, and R$^9$ is selected from the group consisting of H, C$_{1-4}$ alkyl aryl, and (C$_{1-4}$ alkyl)aryl; if A=NR$^9$ the R$^9$ groups may be the same or different;

R$^2$ is selected from the group consisting of hydrogen and C$_{1-6}$ alkyl;

$R^3$ is selected from the group consisting of $C_{1-6}$ alkyl-$R^6$, aryl-$R^6$, cyclo($C_{3-6}$)alkyl-$R^6$, $C_{1-6}$ alkyl-aryl-$R^6$, and $C_{1-6}$ alkyl-cyclo ($C_{3-6}$) alkyl-$R^6$, and $R^6$ is an amidino or guanidino group;

X is $NR^4R^5$ where $R^4$ is selected from the group consisting of hydrogen, aryl, cyclo($C_{3-6}$)alkyl, and $C_{1-6}$ alkyl-cyclo($C_{3-6}$)alkyl; and $R^5$ is hydrogen or $C_{1-6}$ alkyl; or $NR^4R^5$ is a ring;

$R^7$ is hydrogen or $R^{10}CO$ where $R^{10}$ is selected from the group consisting of $C_{1-4}$ alkyl, $C_{1-4}$ alkylaryl, cyclo ($C_{3-6}$)alkyl, $C_{1-4}$ alkyl-cyclo($C_{3-6}$)alkyl, $C_{2-6}$ alkenyl, $C_{2-6}$ alkenyl-aryl, and aryl;

$R^8$ is $C_{1-4}$ alkyl-$R^{11}$;

$R^{11}$ is phthalimido;

$R^{12}$ is hydrogen or is selected from the group consisting of $COR^9$, $CO_2R^9$ (where $R^9$ is not H), $CONHR^9$, and $SO_2R^9$ (where $R^9$ is not H); and $R^{13}$ is selected from the group consisting of OH, $OC_{1-4}$ alkyl, aryl, and $C_{1-4}$ alkylaryl;

or a salt, solvate, or hydrate thereof.

2. The compound, according to claim 1, wherein $R^1$ is $C_{1-6}$ alkyl or $C_{1-6}$ alkyl-$AR^9$, and A is O or $S(O)_{0-2}$.

3. The compound, according to claim 1, wherein $R^2$ is H.

4. The compound, according to claim 1, wherein $R^3$ is selected from the group consisting of $C_{1-6}$ alkyl-$R^6$, aryl-$R^6$, and $C_{1-6}$ alkylaryl-$R^6$.

5. The compound, according to claim 1, wherein $R^4$ is aryl.

6. The compound, according to claim 1, wherein $R^5$ is H.

7. The compound, according to claim 1, wherein $R^8$ is $C_{1-4}$ alkyl-$R^{11}$.

8. The compound, according to claim 1, wherein $R^9$ is selected from the group consisting of H, $C_{1-4}$ alkyl and $C_{1-4}$ alkylaryl.

9. The compound, according to claim 1, wherein $R^{10}$ is $C_{1-4}$ alkyl or aryl.

10. The compound, according to claim 1, wherein $R^{13}$ is OH or $OC_{1-4}$ alkyl.

11. The compound, according to claim 1, selected from the group consisting of:

N-(2-mercapto-5-phthalimidopentanoyl)-L-leucyl-L-argininamide;

N-(2-mercapto-5-phthalimidopentanoyl)-L-isoleucyl-L-argininamide;

N-(2-mercapto-5-phthalimidopentanoyl)-L-norvalyl-L-argininamide; and

N-(2-mercapto-5-phthalimidopentanoyl)-L-valyl-L-argininamide.

12. The compound, according to claim 1, in the form of a single enantiomer or diastereomer.

13. A pharmaceutical composition for use in therapy, comprising a compound of claim 1, and a pharmaceutically acceptable diluent, or carrier.

14. A method for treating a condition associated with matrix metalloproteinases or that is mediated by TNFα or L-selectin sheddase which comprises administering an effective amount of a compound of claim 1.

15. The method, according to claim 14, wherein the condition is selected from the group consisting of cancer, inflammation and inflammatory disease, dermatological disorders, fever, cardiovascular effects, haemorrhage, coagulation and acute phase response, cachexia, anorexia, acute infection, HIV infection, shock states, graft versus host reactions, autoimmune disease, reperfusion injury, meningitis, and migraine.

16. The method, according to claim 14, wherein the condition is selected from the group consisting of tumour growth, angiogenesis, tumour invasion and spread, metastases, malignant ascites, and malignant pleural effusion.

17. The method, according to claim 14, wherein the condition is selected from the group consisting of cerebral ischaemia, ischaemic heart disease, rheumatoid arthritis, osteoarthritis, osteoporosis, asthma, multiple sclerosis, neurodegeneration, Alzheimer's disease, atherosclerosis, stroke, vasculitis, Crohn's disease, and ulcerative colitis.

18. The method, according to claim 14, wherein the condition is selected from the group consisting of corneal ulceration, retinopathy, and surgical wound healing.

19. The method, according to claim 14, wherein the condition is selected from the group consisting of psoriasis, atopic dermatitis, chronic ulcers, and epidermolysis bullosa.

20. The method, according to claim 14, wherein the condition is selected from the group consisting of periodontitis and gingivitis.

21. The method, according to claim 14, wherein the condition is selected from rhinitis, allergic conjunctivitis, eczema, and anaphylaxis.

22. The method, according to claim 14, wherein the condition is selected from the group consisting of restenosis, congestive heart failure, endometriosis, atherosclerosis, and endosclerosis.

* * * * *

UNITED STATES PATENT AND TRADEMARK OFFICE
CERTIFICATE OF CORRECTION

PATENT NO. : 5,872,146
DATED : Feb. 16, 1999
INVENTOR(S) : Andrew Douglas Baxter, et al It is certified that error appears in the above-identified patent and that said Letters Patent is hereby corrected as shown below:

*In the Claims*

Column 13, line 31: "$C_{1-4}$ alkyl" should read --$C_{1-3}$ alkyl--.

Signed and Sealed this

Twenty-seventh Day of July, 1999

Attest:

Q. TODD DICKINSON

*Attesting Officer*     *Acting Commissioner of Patents and Trademarks*